(12) United States Patent
Shuros et al.

(10) Patent No.: US 10,173,067 B2
(45) Date of Patent: *Jan. 8, 2019

(54) VARIABLE SHORTENING OF AV DELAY FOR TREATMENT OF CARDIAC DISEASE

(71) Applicant: Cardiac Pacemakers, Inc., St. Paul, MN (US)

(72) Inventors: Allan Charles Shuros, St. Paul, MN (US); Donald L. Hopper, Maple Grove, MN (US); Shantha Arcot-Krishnamurthy, Vadnais Heights, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 75 days.

This patent is subject to a terminal disclaimer.

(21) Appl. No.: 14/619,316

(22) Filed: Feb. 11, 2015

(65) Prior Publication Data

US 2015/0151127 A1 Jun. 4, 2015

Related U.S. Application Data

(63) Continuation of application No. 11/903,758, filed on Sep. 25, 2007, now Pat. No. 8,972,007.

(51) Int. Cl.
*A61N 1/365* (2006.01)
*A61N 1/368* (2006.01)
*A61N 1/362* (2006.01)

(52) U.S. Cl.
CPC ......... *A61N 1/3682* (2013.01); *A61N 1/3627* (2013.01); *A61N 1/36514* (2013.01); *A61N 1/36535* (2013.01); *A61N 1/36585* (2013.01); *A61N 1/3688* (2013.01)

(58) Field of Classification Search
None
See application file for complete search history.

(56) References Cited

U.S. PATENT DOCUMENTS

| 3,943,936 A | 3/1976 | Rasor et al. |
| 4,884,575 A | 12/1989 | Sanders |
| 5,024,222 A | 6/1991 | Thacker |
| 5,411,535 A | 5/1995 | Fujii et al. |

(Continued)

FOREIGN PATENT DOCUMENTS

| JP | 2001501490 A | 2/2001 |
| JP | 200433742 A | 2/2004 |

(Continued)

OTHER PUBLICATIONS

"U.S. Appl. No. 11/559,131, Final Office Action dated May 10, 2011", 12 pgs.

(Continued)

*Primary Examiner* — Erica Lee
(74) *Attorney, Agent, or Firm* — Schwegman Lundberg & Woessner, P.A.

(57) ABSTRACT

An implantable pacing device for delivering ventricular pacing may be configured to intermittently and variably reduce the AV delay interval used in an atrial triggered pacing mode in a manner that simulates exercise. The device may be programmed to intermittently switch to and from a variably shortened AV delay mode according to defined entry and exit conditions.

20 Claims, 4 Drawing Sheets

(56) References Cited

U.S. PATENT DOCUMENTS

| | | | |
|---|---|---|---|
| 5,466,245 A | 11/1995 | Spinelli et al. | |
| 5,487,752 A | 1/1996 | Salo et al. | |
| 5,919,209 A | 7/1999 | Schouten | |
| 6,208,900 B1 | 3/2001 | Ecker et al. | |
| 6,253,107 B1 | 6/2001 | Albrecht et al. | |
| 6,498,950 B1 | 12/2002 | Bradley | |
| 6,507,756 B1 | 1/2003 | Heynen et al. | |
| 6,553,259 B2 | 4/2003 | Mouchawar et al. | |
| 6,580,946 B2 | 6/2003 | Struble | |
| 6,628,988 B2 | 9/2003 | Kramer et al. | |
| 6,859,667 B2 | 2/2005 | Goode, Jr. | |
| 6,875,180 B2 | 4/2005 | Weiner et al. | |
| 6,912,422 B1 | 6/2005 | Obel | |
| 7,016,726 B1 | 3/2006 | Picardo et al. | |
| 7,065,405 B2 | 6/2006 | Pastore et al. | |
| 7,139,613 B2 | 11/2006 | Reinke et al. | |
| 7,164,946 B2 | 1/2007 | Amblard | |
| 7,177,698 B2 | 2/2007 | Klosterman et al. | |
| 7,184,835 B2 | 2/2007 | Kramer et al. | |
| 7,194,307 B2 | 3/2007 | Salo et al. | |
| 7,203,540 B2 | 4/2007 | Ding et al. | |
| 7,215,997 B2 | 5/2007 | Yu et al. | |
| 7,363,077 B1 | 4/2008 | Min et al. | |
| 7,383,086 B2 | 6/2008 | Ding | |
| 7,392,084 B2 | 6/2008 | KenKnight et al. | |
| 7,539,539 B1* | 5/2009 | Bharmi | A61B 5/0452 600/529 |
| 8,019,416 B2 | 9/2011 | Pastore et al. | |
| 2003/0083700 A1 | 5/2003 | Hill | |
| 2003/0149456 A1 | 8/2003 | Rottenberg et al. | |
| 2004/0093034 A1 | 5/2004 | Girouard et al. | |
| 2004/0243192 A1* | 12/2004 | Hepp | A61N 1/36585 607/17 |
| 2004/0260348 A1 | 12/2004 | Bakken et al. | |
| 2005/0043644 A1 | 2/2005 | Stahmann et al. | |
| 2005/0065554 A1 | 3/2005 | KenKnight et al. | |
| 2005/0096705 A1 | 5/2005 | Pastore et al. | |
| 2005/0107837 A1 | 5/2005 | Salo et al. | |
| 2005/0137630 A1 | 6/2005 | Ding et al. | |
| 2005/0137631 A1* | 6/2005 | Yu | A61N 1/365 607/9 |
| 2006/0036290 A1 | 2/2006 | Hopper et al. | |
| 2006/0122679 A1 | 6/2006 | Wengreen et al. | |
| 2006/0167334 A1* | 7/2006 | Anstadt | A61M 1/106 600/17 |
| 2006/0224225 A1 | 10/2006 | Ransbury et al. | |
| 2006/0241706 A1 | 10/2006 | Yonce et al. | |
| 2006/0253156 A1* | 11/2006 | Pastore | A61N 1/365 607/9 |
| 2006/0287684 A1 | 12/2006 | Baynham et al. | |
| 2008/0114407 A1 | 5/2008 | Pastore et al. | |
| 2008/0114408 A1 | 5/2008 | Shuros et al. | |
| 2008/0119904 A1 | 5/2008 | Salo et al. | |
| 2008/0140146 A1* | 6/2008 | Garner | A61N 1/3712 607/27 |
| 2011/0319955 A1 | 12/2011 | Pastore et al. | |

FOREIGN PATENT DOCUMENTS

| | | |
|---|---|---|
| WO | WO-9743001 A1 | 11/1997 |
| WO | WO-0130443 A1 | 5/2001 |
| WO | WO-0176689 A2 | 10/2001 |
| WO | WO-2006069322 A2 | 6/2006 |
| WO | WO-2006069323 A1 | 6/2006 |
| WO | WO-2008063470 A1 | 5/2008 |
| WO | WO-2008079370 A1 | 7/2008 |

OTHER PUBLICATIONS

"U.S. Appl. No. 11/559,131, Final Office Action dated Jun. 23, 2010", 13 pgs.

"U.S. Appl. No. 11/559,131, Final Office Action dated Jul. 10, 2009", 10 pgs.

"U.S. Appl. No. 11/559,131, Final Office Action dated Dec. 22, 2011", 13 pgs.

"U.S. Appl. No. 11/559,131, Non Final Office Action dated Dec. 23, 2010", 12 pgs.

"U.S. Appl. No. 11/559,131, Non-Final Office Action dated Dec. 29, 2008", 15 pgs.

"U.S. Appl. No. 11/559,131, Non-Final Office Action dated Dec. 31, 2009", 11 pgs.

"U.S. Appl. No. 11/559,131, Pre-Appeal Brief Request filed Aug. 10, 2011", 5 pgs.

"U.S. Appl. No. 11/559,131, Response filed Mar. 30, 2009 to Non Final Office Action dated Dec. 29, 2008", 9 pgs.

"U.S. Appl. No. 11/559,131, Response filed Mar. 31, 2010 to Non Final Office Action dated Dec. 31, 2009", 8 pgs.

"U.S. Appl. No. 11/559,131, Response filed Apr. 25, 2011 to Non Final Office Action dated Dec. 23, 2010", 9 pgs.

"U.S. Appl. No. 11/559,131, Response filed Sep. 23, 2010 to Final Office Action dated Jun. 23, 2010", 8 pgs.

"U.S. Appl. No. 11/559,131, Response filed Oct. 13, 2009 to Final Office Action dated Jul. 10, 2009", 9 pgs.

"U.S. Appl. No. 11/615,383, Final Office Action dated Mar. 12, 2010", 14 pgs.

"U.S. Appl. No. 11/615,383, Non-Final Office Action dated Feb. 5, 2009", 13 pgs.

"U.S. Appl. No. 11/615,383, Notice of Allowance dated May 11, 2011", 5 pgs.

"U.S. Appl. No. 11/615,383, Notice of Allowance dated Dec. 30, 2010", 7 pgs.

"U.S. Appl. No. 11/615383, Notice of Non-Compliant Amendment dated Sep. 18, 2009", 3 pgs.

"U.S. Appl. No. 11/615,383, Response filed May 7, 2009 to Non Final Office Action dated Feb. 5, 2009", 7 pgs.

"U.S. Appl. No. 11/615,383, Response filed Aug. 12, 2010 to Final Office Action dated Mar. 12, 2010", 9 pgs.

"U.S. Appl. No. 11/615,383, Response filed Oct. 19, 2009 to Notice of Non-Compliant Amendment dated Sep. 18, 2009", 7 pgs.

"U.S. Appl. No. 11/903,758, Final Office Action dated Jul. 20, 2010", 15 pgs.

"U.S. Appl. No. 11/903,758, Non Final Office Action dated Apr. 1, 2014", 12 pgs.

"U.S. Appl. No. 11/903,758, Non-Final Office Action dated Dec. 21, 2009", 9 pgs.

"U.S. Appl. No. 11/903,758, Notice of Allowance dated Oct. 24, 2014", 5 pgs.

"U.S. Appl. No. 11/903,758, Response filed Apr. 21, 2010 to Non Final Office Action dated Dec. 21, 2009", 10 pgs.

"U.S. Appl. No. 11/903,758, Response filed Oct. 20, 2010 to Final Office Action dated Jul. 20, 2010", 11 pgs.

"U.S. Appl. No. 13/229,948, Notice of Allowance dated Jul. 10, 2012", 8 pgs.

"Australian Application Serial No. 2007322172, First Examiner Report dated Dec. 1, 2010", 4 pgs.

"Australian Application Serial No. 2007322172, Response filed Dec. 1, 2011 to Office Action dated Dec. 1, 2010", 13 pgs.

"Australian Application Serial No. 2007338688, First Examiner Report dated May 27, 2010", 4 Pgs.

"Australian Application Serial No. 2007338688, Response filed May 13, 2011 to First Examiner Report dated May 27, 2010", 16 pgs.

"Australian Application Serial No. 2011244972, Response filed Jul. 4, 2012 to Office Action dated May 14, 2012", 1 pg.

"Australian Divisional Application Serial No. 2011244972, Non Final Office Action dated May 14, 2012", 2.

"European Application Serial No. 07853460.9, Office Action dated Aug. 6, 2010", 5 pgs.

"European Application Serial No. 07853460.9, Response filed Jan. 25, 2011 to Office Action dated Aug. 6, 2010", 9 pgs.

"European Application Serial No. 07861949.1, Office Action dated Jun. 2, 2010", 3 pgs.

"European Application Serial No. 07861949.1, Response filed Dec. 9, 2010 to Office Action dated Jun. 2, 2010", 11 pgs.

"International Application Serial No. PCT/US20071026235, International Search Report dated Apr. 7, 2008", 4 pgs.

(56) References Cited

OTHER PUBLICATIONS

"International Application Serial No. PCT/US20071026235, Written Opinion dated Apr. 7, 2008", 8 pgs.
"Japanese Application Serial No. 2009-542955, Office Action dated Nov. 28, 2011", (w/ English Translation), 4 pgs.
"Japanese Application Serial No. 2009-542955, Response filed Mar. 28, 2012 to Office Action dated Nov. 18, 2011", (w/ English Translation of Claims), 9 pgs.
"PCT Application Serial No. PCT/US2007/023769, International Search Report dated Mar. 20, 2008", 4 pgs.
"PCT Application Serisl No. PCT/US2007/023769, Written Opinion dated Mar. 20, 2008", 8 pgs.
Adamopoulos, S., "Effects of pulsed beta-stimulant therapy on beta-adrenoceptors and chronotropic responsiveness in chronic heart failure.", Lancet, 345(8946), (Feb. 11, 1995), 344-9.
Coats, A. J., "Controlled trial of physical training in chronic heart failure. Exercise performance, hernodynamics, ventilation, and autonomic function.", Circulation, 85(6), (Jun. 1992), 2119-31.
Goldsmith, R., et al., "Exercise and autonomic function.", Coron Artery Dis, 11(2), (Mar. 2000), 129-35.
Koizumi, T., "Improvement of left ventricular dysfunction during exercise by walking in patients with successful percutaneous coronary intervention for acute myocardial infarction.", Circ J., 67(3), (Mar. 2003), 233-7.

Leier, C. V., "Drug-induced conditioning in congestive heart failure.", Circulation, 65(7), (Jun. 1982), 1382-7.
Liang, C., "Conditioning effects of chronic infusions of dobutamine. Comparison with exercise training.", Journal of Clinical Investigation, 64(2), (Aug. 1979), 613-9.
Myers, J. "Exercise training and myocardial remodeling in patients with reduced ventricular function: one-year follow-up with magnetic resonance imaging", Am Heart J., 139(2), (Feb. 2000), 252-61.
Nakamoto, T., et al., "Beat-to-beat modulation of atrioventricular conduction during dynamic exercise in humans", Japanese Journal of Physiology, vol. 55, (Feb. 2005), 37-51.
Nakamoto, T., et al., "Variability of ventricular excitation interval does not reflect fluctuation in atrial excitation interval during exercise in humans: AV nodal function as stabilizer." J Physiol Sci., 56(1), (Feb. 2006), 67-77.
Prinzen, Frits W, "Mapping of regional myocardial strain and work during ventricular pacing: experimental study using magnetic resonance imaging tagging", Journal of the American College of Cardiology, 33(6), (May 1999), 1735-1742.
Weaver, et al., "Pulmonary Edema Associated with Hyperbaric Oxygen Therapy", Chest, 120, (2001), 1407-1409.
Wolfel, E. E., "Marathoners or couch potatoes: what is the role of exercise in the management of heart failure?", Current Heart Failure Reports, 2(1), (Mar. 2005), 25-34.

* cited by examiner

US 10,173,067 B2

VARIABLE SHORTENING OF AV DELAY FOR TREATMENT OF CARDIAC DISEASE

CLAIM OF PRIORITY

This application is a continuation of U.S. application Ser. No. 11/903,758, filed Sep. 25, 2007, now U.S. Pat. No. 8,972,007 which is hereby incorporated by reference in its entirety.

RELATED APPLICATIONS

This application is related to co-pending U.S. patent application Ser. No. 11/615,383, now issued as U.S. Pat. No. 8,019,416, and Ser. No. 11/559,131, abandoned, the disclosures of which are hereby incorporated by reference.

FIELD OF THE INVENTION

This invention pertains to apparatus and methods for the treatment of heart disease and to devices providing electro-stimulation to the heart such as cardiac pacemakers.

BACKGROUND

Heart failure (HF) is a debilitating disease that refers to a clinical syndrome in which an abnormality of cardiac function causes a below normal cardiac output that can fall below a level adequate to meet the metabolic demand of peripheral tissues. Heart failure can be due to a variety of etiologies with ischemic heart disease being the most common. Inadequate pumping of blood into the arterial system by the heart is sometimes referred to as "forward failure," with "backward failure" referring to the resulting elevated pressures in the lungs and systemic veins which lead to congestion. Backward failure is the natural consequence of forward failure as blood in the pulmonary and venous systems fails to be pumped out. Forward failure can be caused by impaired contractility of the ventricles due, for example, to coronary artery disease, or by an increased afterload (i.e., the forces resisting ejection of blood) due to, for example, systemic hypertension or valvular dysfunction. One physiological compensatory mechanism that acts to increase cardiac output is due to backward failure which increases the diastolic filling pressure of the ventricles and thereby increases the preload (i.e., the degree to which the ventricles are stretched by the volume of blood in the ventricles at the end of diastole). An increase in preload causes an increase in stroke volume during systole, a phenomena known as the Frank-Starling principle. Thus, heart failure can be at least partially compensated by this mechanism but at the expense of possible pulmonary and/or systemic congestion.

When the ventricles are stretched due to the increased preload over a period of time, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium which leads to alterations in cellular structure, a process referred to as ventricular remodeling. Ventricular remodeling leads to further dysfunction by decreasing the compliance of the ventricles (thereby increasing diastolic filling pressure to result in even more congestion) and causing eventual wall thinning that causes further deterioration in cardiac function. It has been shown that the extent of ventricular remodeling is positively correlated with increased mortality in HF patients.

A myocardial infarction (MI) is the irreversible damage done to a segment of heart muscle by ischemia, where the myocardium is deprived of adequate oxygen and metabolite removal due to an interruption in blood supply. It is usually due to a sudden thrombotic occlusion of a coronary artery, commonly called a heart attack. If the coronary artery becomes completely occluded and there is poor collateral blood flow to the affected area, a transmural or full-wall thickness infarct can result in which much of the contractile function of the area is lost. Over a period of one to two months, the necrotic tissue heals, leaving a scar. The most extreme example of this is a ventricular aneurysm, where all of the muscle fibers in the area are destroyed and replaced by fibrous scar tissue. Even if the ventricular dysfunction as a result of the infarct is not immediately life-threatening, a common sequela of a transmural myocardial infarction, or any major MI, especially in the left ventricle, is heart failure brought about by ventricular remodeling in response to the hemodynamic effects of the infarct that causes changes in the shape and size of the ventricle. The remodeling is initiated in response to a redistribution of cardiac stress and strain caused by the impairment of contractile function in the infarcted area as well as in nearby and/or interspersed viable myocardial tissue with lessened contractility due to the infarct. Following an MI, the infarcted area includes tissue undergoing ischemic necrosis and is surrounded by normal myocardium. Until scar tissue forms and even after it forms, the area around the infarcted area is particularly vulnerable to the distending forces within the ventricle and undergoes expansion over a period of hours to days. Over the next few days and months after scar tissue has formed, global remodeling and chamber enlargement occur due to complex alterations in the architecture of the ventricle involving both infarcted and non-infarcted areas. It has been found that the extent of left ventricular remodeling in the late period after an infarction, as represented by measurements of end-systolic and end-diastolic left ventricular volumes, is an even more powerful predictor of subsequent mortality than the extent of coronary artery disease.

Remodeling is thought to be the result of a complex interplay of hemodynamic, neural, and hormonal factors that occur primarily in response to myocardial wall stress. As noted above, one physiological compensatory mechanism that acts to increase cardiac output is increased diastolic filling pressure of the ventricles as an increased volume of blood is left in the lungs and venous system, thus increasing preload. The ventricular dilation resulting from the increased preload causes increased ventricular wall stress at a given systolic pressure in accordance with Laplace's law. Along with the increased pressure-volume work done by the ventricle, this acts as a stimulus for compensatory hypertrophy of the ventricular myocardium. Hypertrophy can increase systolic pressures but, if the hypertrophy is not sufficient to meet the increased wall stress, further and progressive dilation results. This non-compensatory dilation causes wall thinning and further impairment in left ventricular function. It also has been shown that the sustained stresses causing hypertrophy may induce apoptosis (i.e., programmed cell death) of cardiac muscle cells. Thus, although ventricular dilation and hypertrophy may at first be compensatory and increase cardiac output, the process ultimately results in further deterioration and dysfunction.

It has long been known that the heart muscle responds favorably to exercise so as to result in greater pumping efficacy. Studies have shown that HF and post-MI patients can improve their cardiac function and prognosis with regular periods of exercise. Many HF and post-MI patients, however, are either debilitated and cannot exercise or do not tolerate exercise well enough to exercise effectively.

DETAILED DESCRIPTION

Figure 1:
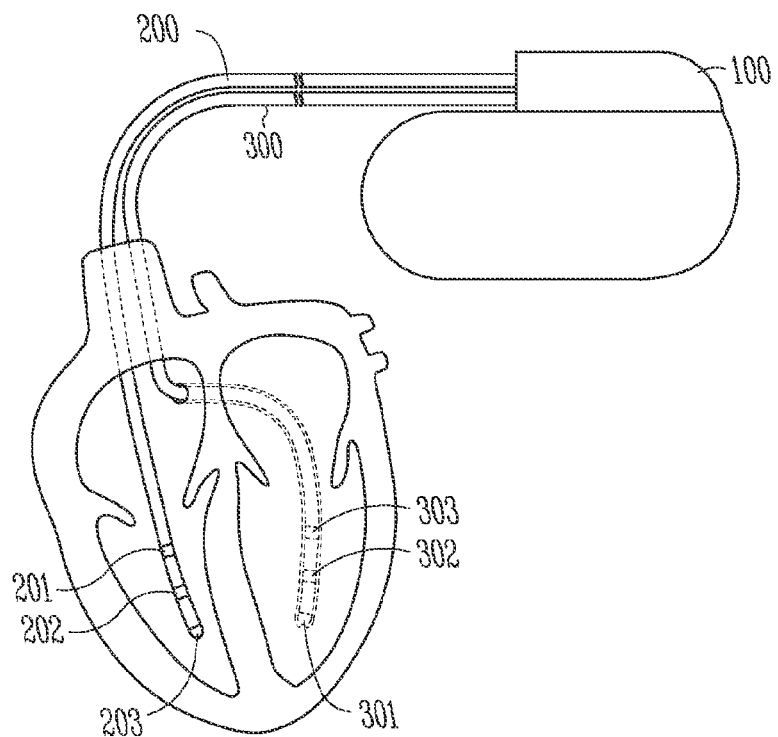
FIG. 1 illustrates the physical configuration of an exemplary pacing device.

Clinical studies have shown that HF and post-MI patients who follow a regular (e.g. 20 min/day, 3 times a week) exercise regimen have symptomatic improvement compared to those who are sedentary. However, not all HF and post-MI patients can exercise due to their cardiac disease or other debilitating conditions. Described herein are methods and devices that use short durations of pacing therapy designed to mimic exercise in order to provide protection from heart failure development and/or attenuation/reversal of cardiac disease progression.

When cardiac output is insufficient to meet the increased metabolic demand, the body responds to the situation with increased activity of the sympathetic nervous system that, among other things, increases heart rate, myocardial contractility, and blood volume. Although acutely beneficial, the long-term effects of increased sympathetic activity are deleterious and lead to ventricular remodeling such as described above. A characteristic feature of chronic cardiac disease is an abnormal autonomic tone with an attenuated level of parasympathetic activity relative to sympathetic activity. When the heart is stressed on a periodic short-term basis, however, such as occurs with regular exercise, the effect is beneficial on both myocardial function and autonomic tone, leading to an increased level of parasympathetic activity. In order to mimic the effects of exercise, pacing therapy can be delivered on a short-term basis in a manner that stresses the heart similar to exercise. Such pacing therapy is referred to herein as simulated exercise pacing. Simulated exercise pacing may generally involve pacing the heart in a manner that temporarily increases cardiac stress levels with or without compromising cardiac output by producing relatively inefficient ventricular contractions and/or some degree of atrio-ventricular dyssynchrony such as described in co-pending U.S. patent application Ser. No. 11/559,131.

In atrial triggered pacing modes (e.g., VDD and DDD modes), a ventricular escape interval is defined between atrial and ventricular events, referred to as the atrio-ventricular delay interval or AVD. The AVD interval is triggered by an atrial sense or pace and stopped by a ventricular sense or pace. A ventricular pacing pulse is delivered upon expiration of the AVD interval if no ventricular sense occurs before. The value of the AVD interval for optimal preloading of the ventricles will vary with heart rate and in a manner that differs from patient to patient. If a patient has a physiologically normal atrial rhythm, ventricular pacing triggered by atrial senses also allows the ventricular pacing rate to be responsive to the metabolic needs of the body. If the atrial rhythm is too slow, the device can be configured to pace the atria on an inhibited demand basis such as in DDD mode which may include rate-adaptive pacing. An atrial escape interval is then defined as the maximum time interval in which an atrial sense must be detected after a ventricular sense or stimulus before an atrial stimulus will be delivered. The lower rate limit interval is then the sum of the atrial escape interval and the AVD interval.

In a patient with normal AV conduction (i.e., no degree of AV block) and normal ventricular function, the optimum AVD that maximizes cardiac output will usually correspond closely with the intrinsic atrio-ventricular interval. When such an AVD is used for normal bradycardia pacing of the ventricles, the ventricular pace is thus delivered close to the time that the ventricles become excited due to intrinsic AV conduction. Similarly, an optimum AVD for resynchronizing the ventricles with biventricular pacing in a patient with intact AV conduction will usually involve pre-exciting the ventricle having the conduction deficit with an AVD that causes that ventricle to contract at roughly the same time that the contralateral ventricle contracts due to intrinsic AV conduction. As described below, employing an AVD for ventricular pacing that is shorter than the intrinsic atrio-ventricular interval (or shorter than the normal intrinsic atrio-ventricular interval in the case of a patient with AV block) is one way of simulating exercise.

Reduction of the AVD primarily results in two things: a reduction in the extent of ventricular pre-loading by the atria and a relatively asynchronous ventricular contraction brought about by the ventricles being excited from one or more ventricular pacing sites with little or no accompanying ventricular excitation via intrinsic AV conduction. Most patients respond negatively to AVD reduction with a relatively compromised cardiac output due to the reduction in atrial preloading and/or the relatively asynchronous and inefficient ventricular contraction resulting from a pace without intrinsic excitation from AV conduction. Delivering ventricular pacing with a reduced AVD to a negatively responding patient produces a relatively asynchronous and inefficient contraction that simulates the stress effects of exercise on the heart. The optimum value of a shortened AVD for producing an asynchronous contraction may vary from patient to patient but would typically be between 10-80 percent of the intrinsic atrio-ventricular interval. An implantable pacing device for delivering ventricular pacing may be configured to intermittently reduce the AVD interval in order to simulate exercise in patients with compromised ventricular function (e.g., HF patients and post-MI patients). The AVD interval may be reduced, referred to herein as an AVD reduction or AVDR mode, by shortening the AVD in an atrial triggered ventricular pacing mode or by switching to a non-atrial triggered ventricular pacing mode (e.g., VVI) and delivering paces at a rate above the intrinsic rate.

It has also been found that the intrinsic atrio-ventricular interval exhibits increased variability during normal exercise. In order to mimic this aspect of normal exercise, the AVD can be variably shortened during what may be called a variably shortened AVD mode or VSAVD mode. Ventricular pacing in a VSAVD mode may delivered on an intermittent basis as controlled by specified entry and exit conditions that could include lapsed time intervals, detection of pulmonary edema, exertion level (e.g., as measured by intrinsic heart rate, activity level, or minute ventilation), patient posture, cardiac output, circadian pattern, disordered breathing patterns (e.g., apnea), and blood pressure. A more detailed description of these techniques is given below after a description of an exemplary cardiac device.

1. Exemplary Cardiac Device

FIG. 1 shows an implantable cardiac device 100 for delivering pacing therapy. Implantable pacing devices are typically placed subcutaneously or submuscularly in a patient's chest with leads threaded intravenously into the heart to connect the device to electrodes disposed within a heart chamber that are used for sensing and/or pacing of the chamber. Electrodes may also be positioned on the epicardium by various means. A programmable electronic controller causes the pacing pulses to be output in response to lapsed time intervals and/or sensed electrical activity (i.e., intrinsic heart beats not as a result of a pacing pulse). The device senses intrinsic cardiac electrical activity through one or more sensing channels, each of which incorporates one or more of the electrodes. In order to excite myocardial tissue in the absence of an intrinsic beat, pacing pulses with energy above a certain threshold are delivered to one or more pacing sites through one or more pacing channels, each of which incorporates one or more of the electrodes. FIG. 1 shows the exemplary device having two leads 200 and 300, each of which is a multi-polar (i.e., multi-electrode) lead having electrodes 201-203 and 301-303, respectively. The electrodes 201-203 are disposed in the right ventricle in order to excite or sense right ventricular or septal regions, while the electrodes 301-303 are disposed in the coronary sinus in order to excite or sense regions of the left ventricle. Other embodiments may use any number of electrodes in the form of unipolar and/or multi-polar leads in order to excite different myocardial sites. As explained below, once the device and leads are implanted, the pacing and/or sensing channels of the device may be configured with selected ones of the multiple electrodes in order to selectively pace or sense a particular myocardial site(s).

Figure 2:
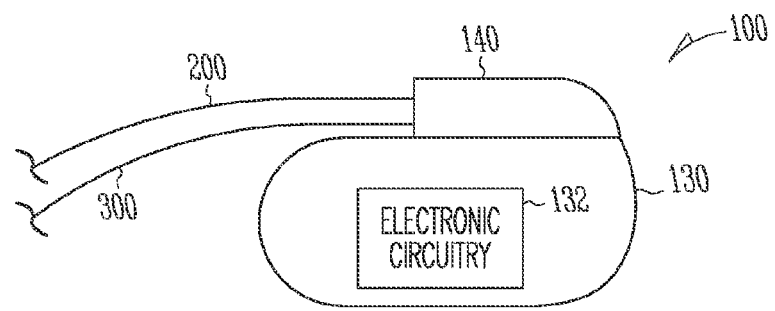
FIG. 2 shows the components of an exemplary device.

FIG. 2 shows the components of the implantable device 100 in more detail. The implantable device 100 includes a hermetically sealed housing 130 that is placed subcutaneously or submuscularly in a patient's chest. The housing 130 may be formed from a conductive metal, such as titanium, and may serve as an electrode for delivering electrical stimulation or sensing in a unipolar configuration. A header 140, which may be formed of an insulating material, is mounted on the housing 130 for receiving leads 200 and 300 which may be then electrically connected to pulse generation circuitry and/or sensing circuitry. Contained within the housing 130 is the electronic circuitry 132 for providing the functionality to the device as described herein which may include a power supply, sensing circuitry, pulse generation circuitry, a programmable electronic controller for controlling the operation of the device, and a telemetry transceiver capable of communicating with an external programmer or a remote monitoring device.

Figure 3:
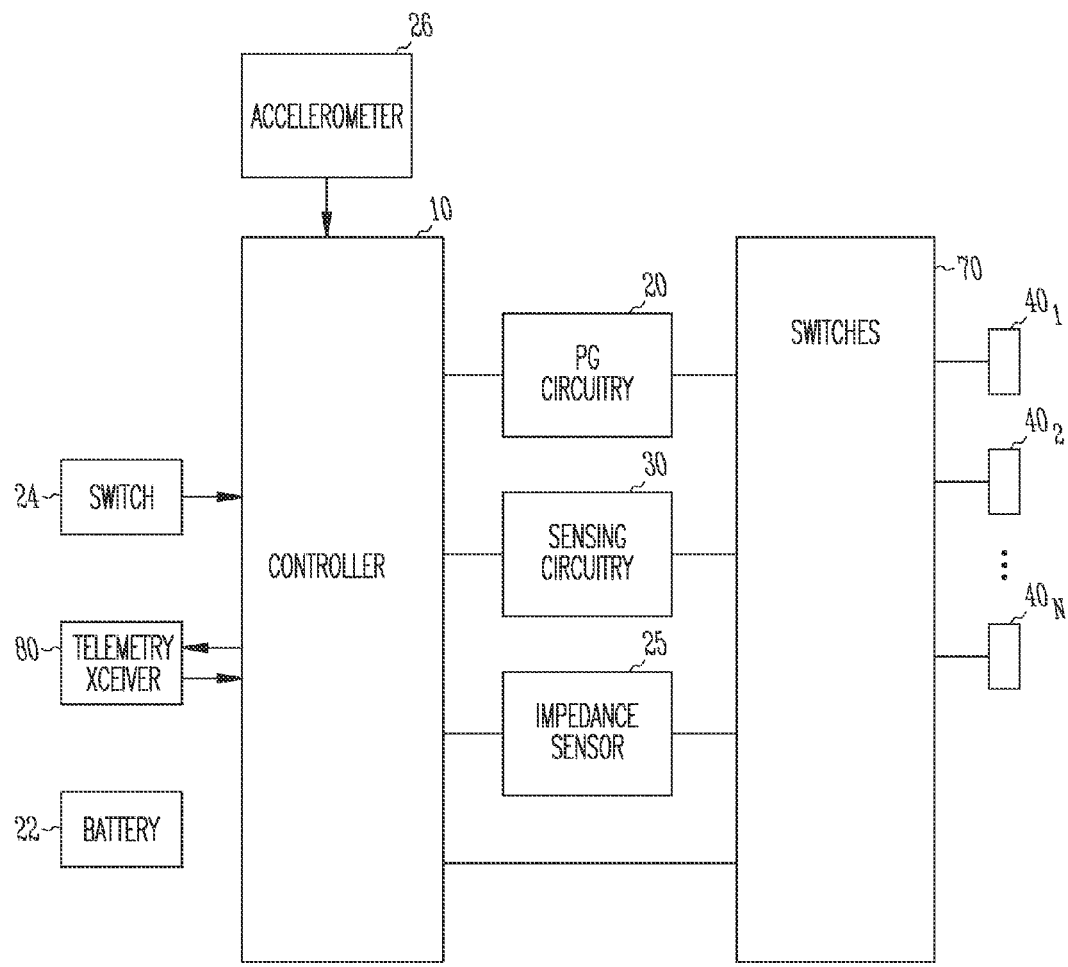
FIG. 3 is a block diagram of the electronic circuitry of an exemplary device.

FIG. 3 shows a system diagram of the electronic circuitry 132. A battery 22 supplies power to the circuitry. The controller 10 controls the overall operation of the device in accordance with programmed instructions and/or circuit configurations. The controller may be implemented as a microprocessor-based controller and include a microprocessor and memory for data and program storage, implemented with dedicated hardware components such as ASIC's (e.g., finite state machines), or implemented as a combination thereof. The controller also includes timing circuitry such as external clocks for implementing timers used to measure lapsed intervals and schedule events. As the term is used herein, the programming of the controller refers to either code executed by a microprocessor or to specific configurations of hardware components for performing particular functions. Interfaced to the controller are sensing circuitry 30 and pulse generation circuitry 20 by which the controller interprets sensing signals and controls the delivery of paces in accordance with a pacing mode. The controller is capable of operating the device in a number of programmed pacing modes which define how pulses are output in response to sensed events and expiration of time intervals. The controller also implements timers derived from external clock signals in order to keep track of time and implement real-time operations such as scheduled AVDR or VSAVD mode pacing.

The sensing circuitry 30 receives atrial and/or ventricular electrogram signals from sensing electrodes and includes sensing amplifiers, analog-to-digital converters for digitizing sensing signal inputs from the sensing amplifiers, and registers that can be written to for adjusting the gain and threshold values of the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The pulse generation circuitry 20 delivers pacing pulses to pacing electrodes disposed in the heart and includes capacitive discharge or current source pulse generators, registers for controlling the pulse generators, and registers for adjusting pacing parameters such as pulse energy (e.g., pulse amplitude and width). The device allows adjustment of the pacing pulse energy in order to ensure capture of myocardial tissue (i.e., initiating of a propagating action potential) by a pacing pulse. The pulse generation circuitry may also include a shocking pulse generator for delivering a defibrillation/cardioversion shock via a shock electrode upon detection of a tachyarrhythmia.

A telemetry transceiver 80 is interfaced to the controller which enables the controller to communicate with an external device such as an external programmer and/or a remote monitoring unit. An external programmer is a computerized device with an associated display and input means that can interrogate the pacemaker and receive stored data as well as directly adjust the operating parameters of the pacemaker. The external device may also be a remote monitoring unit that may be interfaced to a patient management network enabling the implantable device to transmit data and alarm messages to clinical personnel over the network as well as be programmed remotely. The network connection between the external device and the patient management network may be implemented by, for example, an internet connection, over a phone line, or via a cellular wireless link. A switch 24 is also shown as interfaced to the controller in this embodiment to allow the patient to signal certain conditions or events to the implantable device. In different embodiments, the switch 24 may be actuated magnetically, tactilely, or via telemetry such as by a hand-held communicator. The controller may be programmed to use actuation of the switch 24 to control the delivery of AVDR or VSAVD mode pacing.

A pacing channel is made up of a pulse generator connected to an electrode, while a sensing channel is made up of a sense amplifier connected to an electrode. Shown in the figure are electrodes $40_1$ through $40_N$ where N is some integer. The electrodes may be on the same or different leads and are electrically connected to a MOS switch matrix 70. The switch matrix 70 is controlled by the controller and is used to switch selected electrodes to the input of a sense amplifier or to the output of a pulse generator in order to configure a sensing or pacing channel, respectively. The device may be equipped with any number of pulse generators, amplifiers, and electrodes that may be combined arbitrarily to form sensing or pacing channels. The device is therefore capable of delivering single-site or multiple site ventricular pacing for purposes of exercise simulation as well as conventional pacing. One or more pacing channels may also be configured, by appropriate lead placement and pulse energy/frequency settings, for delivering electrical stimulation to stimulate sympathetic and/or parasympathetic nerves. For example, a lead with a stimulation electrode may be placed in proximity to the vagus nerve in order to stimulate that nerve and increase parasympathetic activity. The switch matrix 70 also allows selected ones of the available implanted electrodes to be incorporated into sensing and/or pacing channels in either unipolar or bipolar configurations. A bipolar sensing or pacing configuration refers to the sensing of a potential or output of a pacing pulse between two closely spaced electrodes, where the two electrodes are usually on the same lead (e.g., a ring and tip electrode of a bipolar lead or two selected electrodes of a multi-polar lead). A unipolar sensing or pacing configuration is where the potential sensed or the pacing pulse output by an electrode is referenced to the conductive device housing or another distant electrode.

The device may also include one or more physiological sensing modalities for use in controlling pacing and/or the initiation/cessation of the AVDR or VSAVD mode. An accelerometer 26 enables the controller to adapt the pacing rate in accordance with changes in the patient's physical activity. In order to detect patient posture for purposes of controlling AVDR or VSAVD mode pacing, the accelerometer 26 may be a multi-axis accelerometer. An impedance sensor 25 may be configured with electrodes for measuring minute ventilation for use in rate adaptive pacing and/or cardiac output for use in controlling the AVDR or VSAVD mode. The impedance sensor 25 may also be configured to detect pulmonary edema by measurement of trans-pulmonary impedance. The device may also include a pressure sensor that may be used, for example, to measure pressure in the pulmonary artery. An accelerometer or acoustic sensor may be used as a heart sound sensor to detect heart sounds.

2. Reduction of AVD to Simulate Exercise

One way of delivering simulated exercise pacing is with an AVDR or VSAVD mode. As described earlier, reducing the AVD causes AV dyssynchrony that decreases the amount of ventricular preloading. Decreasing the ventricular preload can decrease cardiac output, and the body may respond to this decrease in a manner similar to its response to exercise. Ventricular pacing with a reduced AVD also causes a relatively asynchronous contraction that can decrease cardiac output to mimic the effects of exercise. The mechanism behind this effect is that when the ventricles are stimulated to contract by a pacing pulse applied through an electrode located at a particular pacing site, the excitation spreads from the pacing site by conduction through the myocardium. This is different from the normal physiological situation, where the spread of excitation to the ventricles from the AV node makes use of the heart's specialized conduction system made up of Purkinje fibers which allows a rapid and synchronous excitation of the entire ventricular myocardium. The excitation resulting from a pacing pulse, on the other hand, produces a relatively asynchronous contraction due to the slower velocity at which the excitation is conducted from the pacing site to the rest of the myocardium. Regions of the myocardium located more distally from the pacing site are also excited later than regions proximal to the pacing site as compared with an intrinsic contraction and subjected to increased mechanical stress. This increased regional stress may elicit cellular changes in the myocardium similar to those caused by stress due to exercise.

Figure 4:
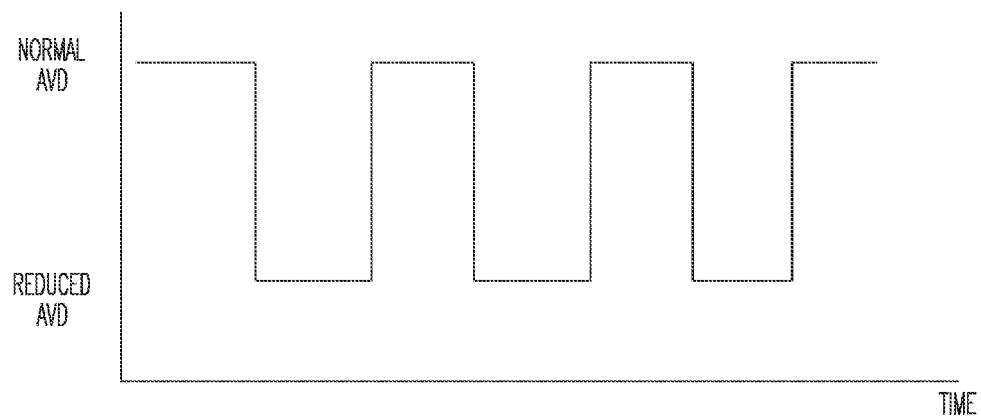
FIG. 4 shows the changes in AV delay as a device periodically enters and exits an AVD reduction mode.
Figure 5:
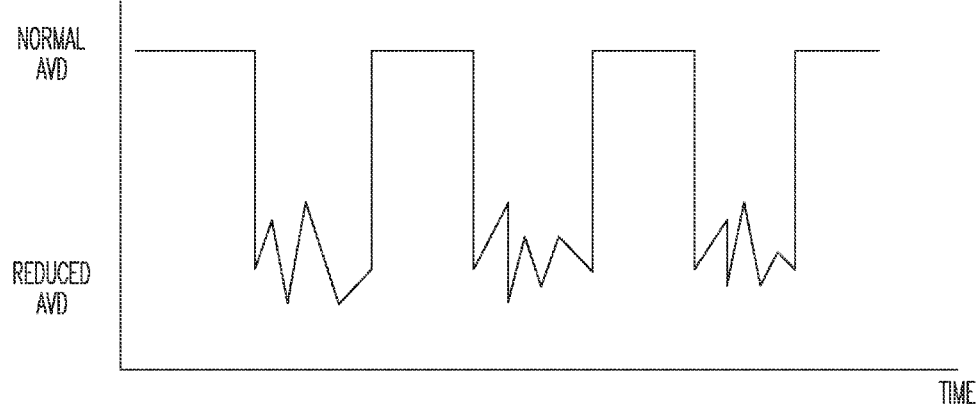
FIG. 5 shows the changes in AV delay as a device periodically enters and exits a variably shortened AVD mode.

As noted above, it has been found that the intrinsic atrio-ventricular interval (PR interval) exhibits increased variability during normal exercise. Such variability in the PR interval tends to counteract variability in the RR interval. In order to more closely duplicate the physiology of normal exercise with simulated exercise pacing, the AVD may be variably shortened in a VSAVD mode. FIGS. 4 and 5 illustrate the differences between an AVDR mode and a VSAVD mode. FIG. 4 shows the time course of changes in AV delay as a device periodically enters and exits an AVD reduction mode, while FIG. 5 shows the time course of changes in AV delay as a device periodically enters and exits a VSAVD mode. In an AVDR mode, the AVD is shortened to some value below the normal AVD where it remains until the mode is exited. In the VSAVD mode, the AVD is shortened to a range of values below the normal AVD, referred to as the reduced AVD range, and the AVD is made to vary within the reduced AVD range while the mode is operative. In the case of a patient with AV block, the AV delay may be made to vary within a range selected from a value shorter than a nominal intrinsic AV delay interval based upon demographic data or a value shorter than a nominal intrinsic AV delay interval based upon hemodynamic measurements. In specific embodiments, the AV delay is made to vary within a range that is 10-80% of the patient's measured intrinsic AV delay interval, 10-80% of a nominal intrinsic AV delay interval based upon demographic data, or 10-80% of a nominal intrinsic AV delay interval based upon hemodynamic measurements. The variation of the AVD during the VSAVD mode may be implemented in a number of different ways. For example, the AVD may be made to vary according to a predetermined sequence of values within the reduced AVD range or according to a pseudo-random sequence of values within the reduced AVD range. Either instead of, or in addition to such prescribed variation, the AVD may be made to vary according to measured parameters that trigger variation of the AVD where the AVD may or may not be constrained to remain within the reduced AVD range. Examples of such triggering parameters include previous PP intervals (i.e., the intervals between atrial senses), previous RR intervals (i.e., the intervals between ventricular senses), measured heart rate variability, patient posture, respiratory inspiration and expiration as detected by a minute ventilation sensor, and hemodynamic parameters such as blood pressure or cardiac stroke volume as measured by an impedance sensor. In the case of respiratory variation, for example, the AVD could be shortened with inspiration and lengthened with expiration.

VSAVD pacing can be delivered to the heart in a way that mimics the beneficial effects of exercise. Chronic simulated exercise pacing, however, could overstress the heart in HF or post-MI patients and could be hazardous. Accordingly, it would ordinarily be preferable to deliver simulated exercise pacing on an intermittent basis. As described below, a pacing device may therefore be configured to switch from a normal operating mode to an VSAVD mode according to some defined exit and entry conditions that cause intermittent operation in the VSAVD mode. Such entry and exit conditions, for example, may define a schedule that specifies switching in response to lapsed time intervals and/or in response to one or more other types of conditions detectable by the device.

3. Implementation of Normal and VSAVD Modes

As defined herein, the VSAVD mode is an atrial triggered ventricular pacing mode (e.g., VDD, DDD, or DDDR) in which ventricular pacing is delivered with a variably shortened AVD. Switching from a normal operating mode to the VSAVD mode may be implemented in a number of ways. If the normal mode does not include delivery of pacing therapy, the VSAVD mode may include delivery of ventricular pacing in an atrial triggered mode with a short and variable AVD. If the normal mode includes atrial triggered pacing with a specified AVD, the VSAVD mode may include ventricular pacing in an atrial triggered mode using an AVD shorter than that used in the normal operating mode and made to vary as described above. For purposes of specifying the reduced AVD range used in the VSAVD mode, the device may be configured to measure the intrinsic atrio-ventricular interval and compute the AVD as a specified percentage thereof. For patients with AV block whose intrinsic atrio-ventricular interval cannot be measured, a reduced AVD may be calculated as a percentage of a nominal intrinsic atrio-ventricular interval. The nominal intrinsic atrio-ventricular interval may be based, for example, upon demographic data reflecting a normal atrio-ventricular interval or based upon individualized value determined from hemodynamic measurements of a particular patient while pacing with different AVD values. When some kind of pacing therapy is delivered in the normal operating mode and the device possesses multiple pacing channels with different pacing sites, the VSAVD mode may involve using either the same or a different pacing channel for delivering ventricular pacing. The VSAVD mode may also involve ventricular pacing at multiple sites and/or switching to different pacing sites during operation of the mode according to some defined schedule.

4. Conditional Entry and Exit into VSAVD Mode

Figure 6:
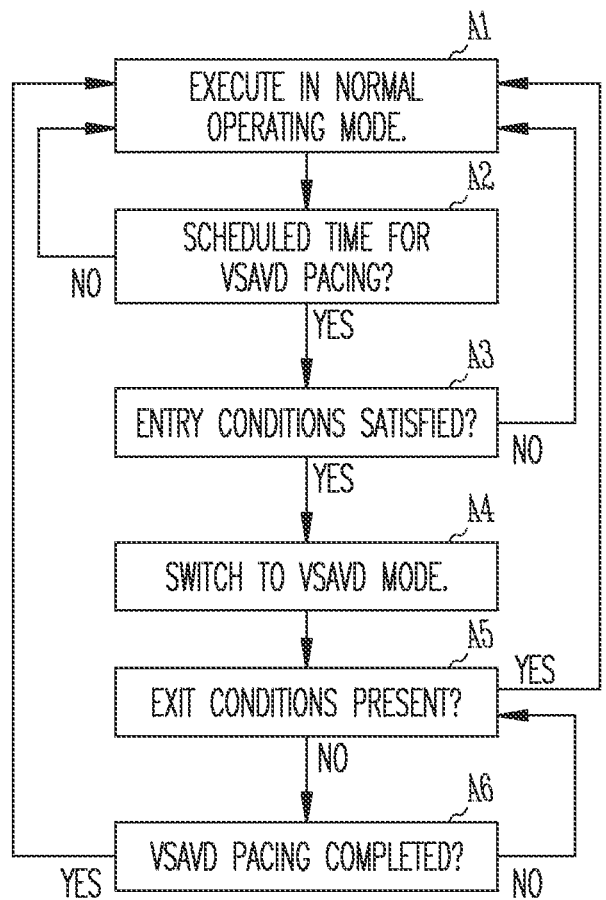
FIG. 6 illustrates an exemplary algorithm for controlling entry and exit into the VSAVDR mode.

The device may be configured to use one or more entry and/or exit conditions in controlling entry and/or exit into the VSAVD mode. An entry or exit condition could be, for example, a lapsed time interval (e.g., specified time(s) of the day), actuation of a switch by the patient (e.g., a magnetically or tactilely actuated switch interfaced to the device controller), a command received via telemetry, detection or non-detection of a condition such as pulmonary edema or a supine posture, or a measured variable being within or out of a specified range. Examples of such measured variables include heart rate, activity level, minute ventilation, cardiac output, heart sounds, and blood pressure. Entry and/or exit conditions may also be composite conditions where a plurality of entry and/or exit conditions are logically ORed or ANDed together to determine whether a composite entry or entry condition is satisfied. FIG. 6 illustrates an exemplary algorithm executable by the device controller for controlling entry and exit into the VSAVD mode. The controller is also programmed to vary the AVD in the manners described above while in the VSAVD mode. In this example, one of the entry conditions is a specified time of the day during which it is desired to delivery VSAVD pacing if other entry conditions are met. As shown in the figure, the controller of the device is programmed to transition through a number of different states, designated as A1 through A6. At state A1, the device operates in its normal operating mode. At state A2, while continuing to operate in state A1, the device determines whether it should switch to the VSAVD mode based upon a lapsed time interval or a triggering condition. Optionally, the device may also be configured to test for one or more particular entry conditions before switching to the simulated exercise mode as implemented by state A3. Examples of entry conditions that must be satisfied before the switch to the VSAVD mode include a measured exertion level being within a specified entry range (where exertion level may be measured by, e.g., heart rate, activity level, or minute ventilation), non-detection of cardiac arrhythmias, non-detection of cardiac ischemia, receipt of a telemetry command, and actuation by the patient of a magnetically or tactilely actuated switch incorporated into the device that allows switching to the VSAVD mode. At state A3, the device checks to see if the one or more entry conditions are satisfied and returns to state A1 if not. If the appropriate entry conditions are satisfied, the device switches to the VSAVD mode at state A4. The VSAVD mode supercedes the normal operating mode to the extent necessary to carry out the VSAVD pacing but may allow certain functions performed in the normal operating mode to continue. Alternatively, the VSAVD mode could be said to incorporate particular functions of the normal operating mode, which functions are modified if necessary to deliver the VSAVD pacing. While executing in the VSAVD mode, the device may be configured to monitor for one or more exit conditions which cause the device to revert to the normal operating mode. Such exit conditions could be the same or different from the entry conditions that must be satisfied before entering the VSAVD mode. At state A5, while executing in the VSAVD mode, the device monitors for the occurrence of one or more exit conditions such as a measured exertion level being outside a specified permissible range, a measured heart rate being outside a specified permissible range, presence of a cardiac arrhythmia, presence of cardiac ischemia, receipt of a telemetry command, and actuation by the patient of a magnetically or tactilely actuated switch incorporated into the device by the patient to stop delivery of VSAVD pacing. If an exit condition occurs, the device returns to the normal operating mode at state A1. Otherwise, the device proceeds to state A6 and checks to see if the prescribed amount and/or duration of VSAVD pacing have been delivered. If the specified amount or duration of VSAVD pacing has been delivered, the device returns to state A1 and resumes the normal operating mode. Otherwise, the device loops back to state A5 to monitor for exit conditions. For example, the device may be programmed to deliver VSAVD pacing that simulates exercise for a prescribed amount of time per day (e.g. 30 min). The time when therapy delivery is started may be random (once per day at a random time), at a specific time each day, or triggered by a specific event (e.g., when the patient falls asleep, the patient wakes up, or the patient's exertion level falls below a certain threshold).

5. Exemplary Implementation Schemes

In an exemplary embodiment, the device is programmed to periodically (e.g., every 24 to 72 hours) switch to the VSAVD mode for some specified period of time, referred to as the AVD reduction period or AVDRP (e.g., 15-60 minutes). If the device delivers some kind of therapy during its normal mode (e.g., for cardiac resynchronization therapy, remodeling control therapy, or bradycardia), the VSAVD mode could be implemented as atrial triggered ventricular pacing (e.g., VDD or DDD) with a shorter AV delay than that used in the normal mode that also varies during the AVDRP. If no pacing is delivered in the normal mode, the AVDR mode could be implemented as atrial triggered ventricular pacing with a specified short and variable AV delay. If the device is equipped with an atrial lead and only a single implanted ventricular lead, the implanted ventricular site would be paced with the reduced and variable AV delay for the entire AVDRP. If the device is equipped with electrodes implanted at multiple ventricular sites (e.g., as multiple leads or as one or multi-polar leads), all or some selected subset of the ventricular pacing sites could be paced during the AVDRP. The ventricular sites could also be rotated during the AVDRP according to a specified duty cycle. For example, if the device has electrodes implanted at two ventricular sites, the AVDR mode could be implemented as VSAVD pacing delivered to a selected one of the sites for entire AVDRP, VSAVD pacing delivered to one site for some percentage (e.g. 50%) of the AVDRP and switching to the other site for the remaining portion of the AVDRP, or VSAVD pacing delivered to both ventricular sites for each paced cycle (either simultaneously or with offset between the two sites) during the entire AVDRP. Similarly, if the device has more than two ventricular leads or more than two ventricular pacing sites (e.g. quadripolar lead), VSAVD pacing could be delivered to a single selected site for the entire AVDRP, VSAVD pacing could be delivered to all of the implanted sites for each paced cycle (either simultaneously or with specified offsets) during the AVDRP, or VSAVD pacing could be rotated from one ventricular site to the next during the AVDRP. For example, if there are four ventricular pacing sites, VSAVD pacing could be delivered to a first site for the first 25% of the AVDRP, to a second site for the next 25% of the AVDRP, etc., where the percentage of time each site is paced may or may not be evenly distributed.

6. Other Embodiments

As described above, VSAVD pacing may be used to simulate exercise by intentionally causing asynchronous ventricular contractions. As described in co-pending U.S. patent application Ser. No. 11/559,131, asynchronous contractions may also be produced in other ways such as by pacing different sites at different times to cause the heart to contract in an inefficient way, and the embodiments described herein may be combined with any of the embodiments described in that application.

The invention has been described in conjunction with the foregoing specific embodiments. It should be appreciated that those embodiments may also be combined in any manner considered to be advantageous. Also, many alternatives, variations, and modifications will be apparent to those of ordinary skill in the art. Other such alternatives, variations, and modifications are intended to fall within the scope of the following appended claims.

What is claimed is:
1. A cardiac device, comprising:
    pulse generation circuitry for delivering pacing pulses to one or more ventricular sites;
    sensing circuitry for receiving electrogram signals from atrial and ventricular electrodes and detecting atrial and ventricular senses;
    a controller interfaced to the pulse generation and sensing circuitry for controlling the operation of the device in accordance with programmed instructions and programmed to operate in either a normal operating mode or a variably shortened AV delay (VSAVD) mode;
    a respiratory sensor interfaced to the controller;
    wherein, in the VSAVD mode, the controller is programmed to deliver ventricular paces to the one or more ventricular sites in an atrial-triggered pacing mode in which the ventricular paces are delivered upon expiration of an AV (atrio-ventricular) delay interval;
    wherein, in the VSAVD mode, the controller is programmed to vary the value of the AV delay interval within a range that is shorter than a patient's measured intrinsic AV delay interval by shortening the AV delay with inspiration and lengthening the AV delay with expiration; and,
    wherein the controller is programmed to switch from the normal operating mode to the VSAVD mode when a measured exertion level is within a specified entry range.

2. The device of claim 1 wherein the controller is programmed to vary the AV delay interval within a range that is shorter than a nominal intrinsic AV delay interval based upon demographic data.

3. The device of claim 2 wherein the range is 10-80% of the nominal intrinsic AV delay interval based upon demographic data.

4. The device of claim 1 wherein the controller is programmed to vary the AV delay interval within a range that is shorter than a nominal intrinsic AV delay interval based upon hemodynamic measurements.

5. The device of claim 4 wherein the range is 10-80% of or the nominal intrinsic AV delay interval based upon hemodynamic measurements.

6. The device of claim 1 wherein the range is 10-80% of the patient's measured intrinsic AV delay interval.

7. The device of claim 1 wherein the controller is programmed to additionally vary the AV delay interval according to a predetermined sequence of values.

8. The device of claim 1 wherein the controller is programmed to additionally vary the AV delay interval according to a pseudo-random sequence of values.

9. The device of claim 1 further comprising a multi-axis accelerometer and wherein the controller is programmed to additionally vary the AV delay interval in accordance with a patient's posture.

10. The device of claim 1 wherein the controller is further configured to, in the VSAVD mode, switch between different ones of the one or more ventricular pacing sites.

11. A method for operating a cardiac pacing device, comprising:
    delivering pacing pulses to one or more ventricular sites;
    receiving electrogram signals from atrial and ventricular electrodes and detecting atrial and ventricular senses;
    operating in either a normal operating mode or a variably shortened AV delay (VSAVD) mode;
    sensing a patient's respiration;
    in the VSAVD mode, delivering ventricular paces to the one or more ventricular sites in an atrial-triggered pacing mode in which the ventricular paces are delivered upon expiration of an AV (atrio-ventricular) delay interval;
    in the VSAVD mode, varying the value of the AV delay interval within a range that is shorter than a patient's measured intrinsic AV delay interval by shortening the AV delay with inspiration and lengthening the AV delay with expiration; and, switching from the normal operating mode to the VSAVD mode when a measured exertion level is within a specified entry range.

12. The method of claim 11 further comprising varying the AV delay interval within a range that is shorter than a nominal intrinsic AV delay interval based upon demographic data.

13. The method of claim 12 wherein the range is 10-80% of the nominal intrinsic AV delay interval based upon demographic data.

14. The method of claim 11 further comprising varying the AV delay interval within a range that is shorter than a nominal intrinsic AV delay interval based upon hemodynamic measurements.

15. The method of claim 14 wherein the range is 10-80% of or the nominal intrinsic AV delay interval based upon hemodynamic measurements.

16. The method of claim 11 wherein the range is 10-80% of the patient's measured intrinsic AV delay interval.

17. The method of claim 11 further comprising varying the AV delay interval according to a predetermined sequence of values.

18. The method of claim 11 further comprising varying the AV delay interval according to a pseudo-random sequence of values.

19. The method of claim 11 further comprising varying the AV delay interval in accordance with a patient's posture.

20. The method of claim 11 further comprising, in the VSAVD mode, switching between different ones of the one or more ventricular pacing sites.

* * * * *